United States Patent [19] [11] 4,093,484
Harrison et al. [45] June 6, 1978

[54] METHOD OF MAKING SURGICAL CATHETERS AND TUBES

[75] Inventors: Reginald William Harrison, Salisbury; George Albert Peach, Andover, both of England

[73] Assignee: Warne Surgical Products Limited, Hampshire, England

[21] Appl. No.: 705,336

[22] Filed: Jul. 14, 1976

[30] Foreign Application Priority Data

July 16, 1975 United Kingdom .............. 29903/75

[51] Int. Cl.² .................... B29D 23/03; B29D 23/04; B32B 31/30
[52] U.S. Cl. ........................... 156/244.13; 128/349 B; 156/245; 156/294; 264/88; 264/94
[58] Field of Search ............... 156/242, 244, 245, 293, 156/294, 500; 128/349 B, 349 R; 264/88, 94, 173, 209

[56] References Cited

U.S. PATENT DOCUMENTS

| 2,230,151 | 1/1941 | Winder | 264/94 |
| 3,295,159 | 1/1967 | Fischer | 264/94 |
| 3,333,036 | 7/1967 | Maurer et al. | 264/88 |
| 3,528,869 | 9/1970 | Dereniuk | 264/94 |
| 3,602,945 | 9/1971 | Pope et al. | 264/94 |

*Primary Examiner*—Caleb Weston
*Attorney, Agent, or Firm*—Wood, Herron & Evans

[57] ABSTRACT

A method of forming a cuff on a self-retaining catheter of the type described comprising fitting a tube of thermoplastic material around the main shaft of the catheter, bonding the ends of the tube to the shaft, surrounding the tube with a mould, inflating the tube and heating the mould.

7 Claims, 10 Drawing Figures

U.S. Patent    June 6, 1978    Sheet 1 of 3    4,093,484
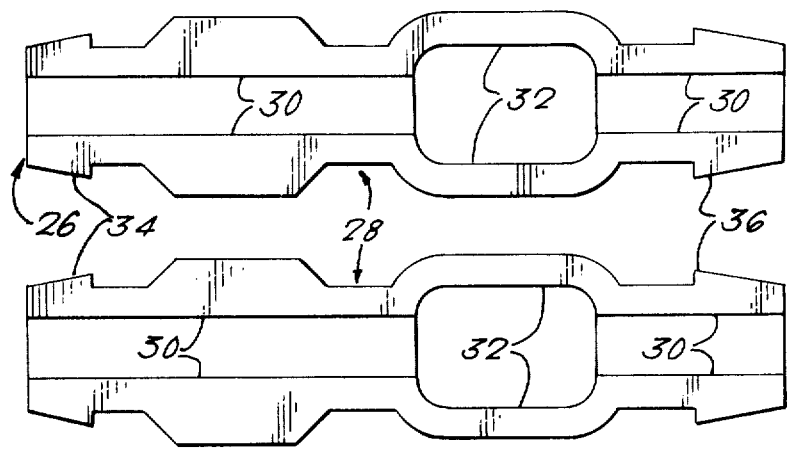
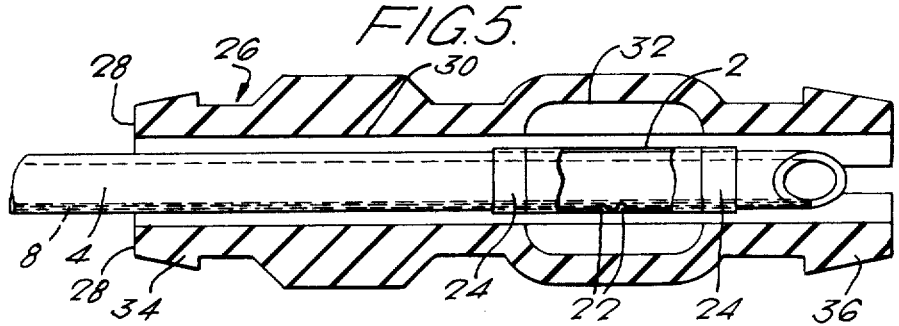
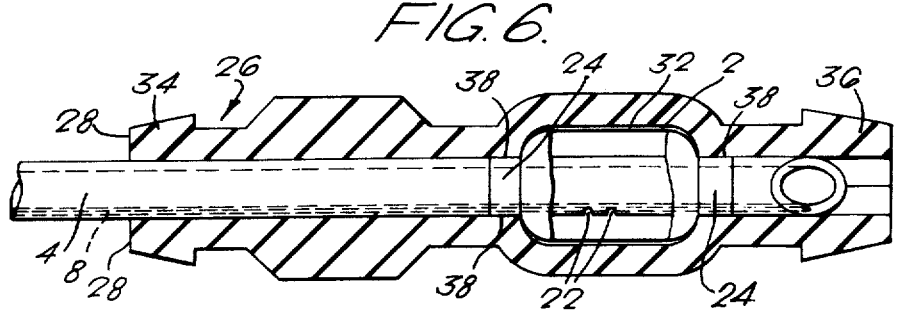

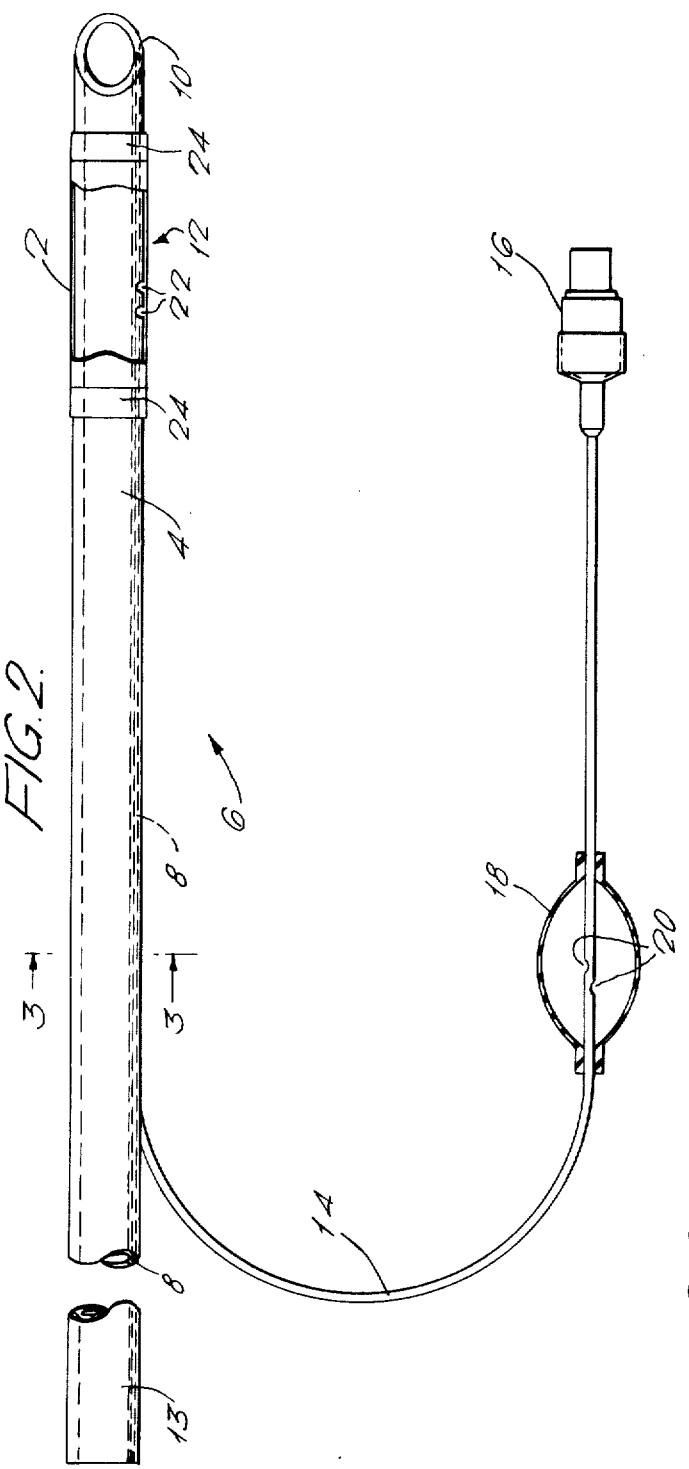
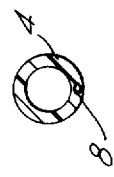

METHOD OF MAKING SURGICAL CATHETERS AND TUBES

This invention relates to improvements in and relating to surgical catheters and tubes.

Surgical catheters and tubes may have shaped thin walled cuffs, fixed around a short length of their main shaft in close proximity to their patient end or tip, the cuff in use being inflated with a suitable medium to hold the catheter in place and/or to act as a seal between the catheter and certain passages of the body, such as, for example in the case of a tracheal tube and the trachea. Such a catheter will hereinafter be referred to as a self-retaining catheter of the type described.

A method of forming a cuff on a self-retaining catheter of the type described, in accordance with the invention, comprises fitting a tube of thermoplastic material around the main shaft of the catheter, bonding the ends of the tube to the shaft, surrounding the tube with a mould, inflating the tube, heating the mould and preferably then cooling the mould.

Inflating the tube causes it to take the shape of the surrounding mould, and the consequent heating, preferably to a temperature of about 100° C, and cooling of the thermoplastic material, which may be poly-vinyl chloride (P.V.C.), causes the tube to retain the shape of the mould, which is the desired shape and size of the cuff.

The main shaft in the area of the tube and/or the mould are preferably pre-heated before fitting the mould desirably to a temperature of about 60° C, to soften the tube and allow it to be more easily inflated to the shape of the mould.

The tube may be initially formed by extruding a thin-walled tubing to form a close fit onto the main shaft of the catheter, and then cutting the tubing to the desired length of the cuff.

Preferably, the tube is inflated by means of air which enters the tube by an inlet tube leading to a capillary passage in the wall of the main shaft of the catheter, the passage opening to the inside of the tube by means of a hole or holes drilled in the outside of the wall of the main shaft of the catheter. The capillary passage which would normally be open at the ends of the shaft, is blocked during manufacture of the shaft to prevent escape of air from these ends. A predetermined amount of air may be injected into the space between the wall of the shaft and the tube forming the cuff via the inlet tube by a known measuring device (e.g. a syringe).

The inlet tube may have a self-retaining valve to prevent premature air loss from the cuff. The inlet tube and capillary passage are standard attachments to many catheters, and are used for inflating the cuff when the catheter is in use.

The invention not only extends to a method of forming a cuff on a self-retaining catheter of the type described, but also to a catheter having a cuff formed thereon by the method of the invention.

A mould for producing a cuff on a self-retaining catheter of the type described, in accordance with the invention, has two halves, each half having a recess, the recesses being arranged to mate to form a space having a size and shape corresponding to the desired size and shape of the cuff when inflated, and an inlet and an outlet to secure the catheter adjacent the position at which the cuff is to be formed.

The invention will now be further described by way of example, with reference to the accompanying drawings, in which:

FIG. 1 is a sketch of a tube to be used to form a cuff by the method of the invention;

FIG. 2 is a sketch of a catheter, known as an endotracheal tube, at one stage in the method of forming a cuff thereon;

FIG. 3 is a cross-section on lines 3—3 of FIG. 2;

FIG. 4 is a diagram of a mould used in forming a cuff in accordance with the invention.

FIGS. 5 and 6 illustrate stages in the method of forming the cuff; and

Figure 7:
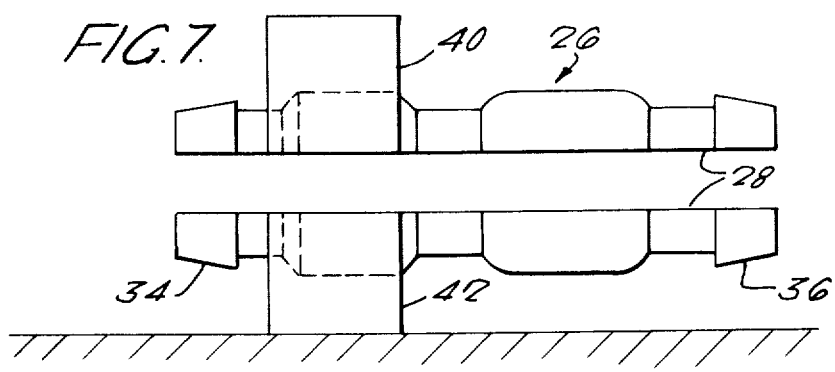
FIGS. 7 to 10 illustrate the mechanical operation of the mould.

A thin walled tube 2, shown in FIG. 1, is formed of thermoplastic material which is resistant to attack by body fluids and anaesthetic gases, and which is capable of being sterilised such as by exposure to ethylene oxide or gamma radiation. A suitable material is poly-vinyl chloride (P.V.C.) having a processing temperature range in the region of about 120° C to 200° C. The tube is formed by extruding thermoplastic material in the form of tubing, and then cutting the tube to the required length, the resultant tubing 2 being of such dimensions that it is close fit on the main shaft 4 of a catheter generally indicated at 6, as shown in FIG. 2.

The catheter 6 has a capilliary passage 8 in its wall extending along the length of the shaft 4 (see also FIG. 3). The passage 8 is blocked, as indicated at 10, at the distal or patient end 12 of the catheter, and also at the opposite end 13. An inlet tube 14 is connected to the shaft 4 of the catheter and communicates with the capilliary passage 8. The other end of the inlet tube 14 is provided with a valve 16, and a pilot balloon 18 is situated around the inlet tube 14 at a position along its length, the interior of the pilot balloon communicating with the interior of the inlet tube 14 by means of holes 20. The tube 14, valve 16 and pilot balloon 18 are known items.

The tube 2 is positioned on the end 12 of the shaft 4 at the correct distance along the length of the shaft and over holes 22 which are cut into the outside wall of the shaft 4 to communicate with the capilliary passage 8. The ends of the tube 2 are then bonded to the wall 4 of the catheter 6 as indicated at 24.

Referring to FIG. 4 a mould 26 comprises two halves 28. The mould is shaped as indicated at 30 to form an inlet and an outlet, which, in use, fits around the shaft 4 of the catheter 6. The mould is also shaped as indicated at 32 to a shape and size corresponding to the desired inflated shape and size of the cuff to be formed. The mould 26 has tapered ends indicated at 34 and 36.

After the tube 2 has been bonded in the correct position to the shaft 4 of the catheter, as shown in FIG. 2, the region of the shaft holding the tube is heated to a temperature of approximately 60° C. The mould is also heated to approximately this temperature. The heating may be achieved by, for example, electrical induction, microwave methods, or a method employing direct heat.

The catheter 6 is then positioned between the two halves 28 of the mould 26, as shown in FIG. 5, with the tube 2 located between the parts of the mould shape as indicated at 32.

The halves 28 of the mould 26 are then closed as shown in FIG. 6. The bonded areas 24 of the tube 2 are held in position by the parts of the mould indicated at 38. A predetermined amount of a fluid, e.g., air is then injected into the space between the shaft 4 of the catheter and the side of the tube 2, by a measuring devices such as, for example, a syringe. The air is injected via valve 16, tube 14, capillary passage 8, and holes 22. This causes the tube 2 to expand. The mould is then heated by, for example, electrical induction, microwaves methods, or a method employing direct heat, to a temperature about 100° C, for about 10 to 20 seconds. This heat then causes the plasticized thermoplastic material of tube 2 to further soften, and the air between the wall 4 of the catheter and the inside of the tube 2 pushes out the tube 2 so that it fully conforms to the shape of the mould indicated at 32. The mould is then cooled by, for example, air, water or refrigerant. This causes the tube 2 to retain the shape of the mould indicated at 32.

The valve 16 may then be opened to relieve the pressure due to the air in the inflated cuff formed by the tube 2. This is preferably done before the catheter is removed from the mould, as otherwise over-inflation of the tube 2 may occur.

Figure 8:
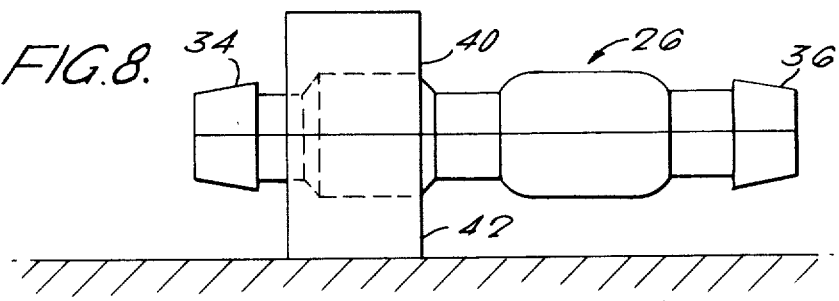
Figure 9:
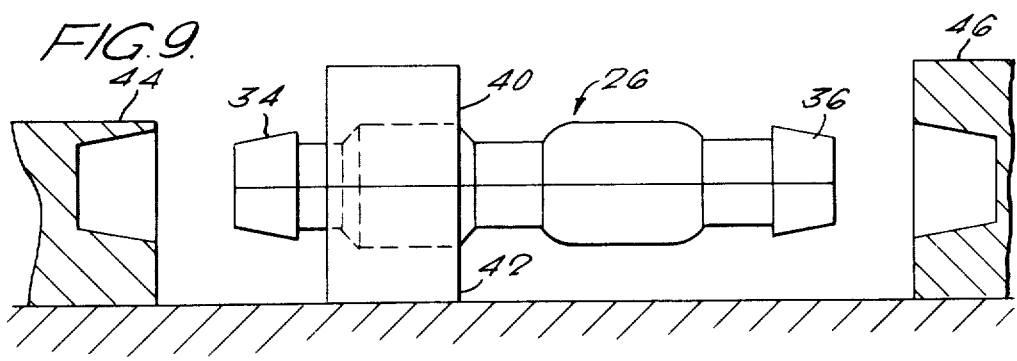
Figure 10:
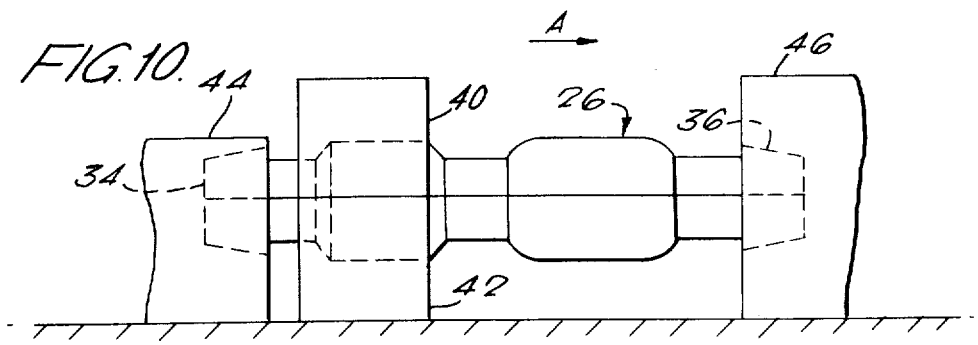

The mechanical operation of the mould is indicated in FIGS. 7 to 10. The halves 28 of the mould 26 are fixed to clamp blocks 40 and 42. The catheter 6 with the tube 2 bonded thereon is then positioned between the halves 28 of the mould, and the mould then closed as indicated in FIG. 8 by lowering the top clamp block 40. Before inserting air into the tube 2, tapered locking blocks 44 and 46 are moved laterally together to lock on tapers 34 and 36 at the ends of the mould 26 to lock the mould in the closed position as indicated in FIGS. 9 and 10. The two blocks 44 and 46 are then both moved in the direction of arrow A to move the catheter in the mould 26 into the area in which it is heated.

This operation is reversed to release the catheter from the mould on completion of the cuff forming process.

We claim:

1. A method of forming a cuff on a self-retaining catheter, said method comprising the steps of providing a catheter having a tubular shaft, a passage extending inside and along the length of the wall of said shaft, and a hole extending between said passage and the outside surface of said shaft in proximity to the distal end of said shaft, extruding a thin-walled tube of thermoplastic material, fitting said tube onto said tubular shaft at the distal end thereof at a position where said tube overlies said hole, bonding the ends of said tube to said tubular shaft, and, thereafter, heating said tube to a first temperature to soften said tube and surrounding said tube with a mould, then injecting a fluid into said tube via said passage and said hole so as to cause said tube to expand and adopt the shape of said mould, then heating said mould to a second temperature higher than said first temperature, said second temperature being sufficient to allow flow of said thermoplastic material, then cooling said mould to cause said tube to retain its expanded shape, and then allowing the fluid in said tube to escape and removing the mould.

2. A method as claimed in claim 1 including the step of heating said tube to said first temperature prior to surrounding said tube with said mould.

3. A method as claimed in claim 1 wherein said first temperature is substantially 60° C.

4. A method as claimed in claim 1 wherein said second temperature is substantially 100° C.

5. A method as claimed in claim 1 including the step of allowing the fluid in said tube to escape before said mould is removed, thereby preventing over-inflation of said tube.

6. A method as claimed in claim 1 including the step of preheating said mould to a temperature substantially equal to said first temperature prior to injecting the fluid into said tube.

7. A method as claimed in claim 6 including the step of surrounding said tube with said preheated mould, said preheated mould serving to heat said tube to said first temperature.

* * * * *